United States Patent [19]
van Hoboken et al.

[11] Patent Number: 5,358,979
[45] Date of Patent: Oct. 25, 1994

[54] PRIMARILY SOLID CONCENTRATE WHICH CONTAINS A BIOCIDE

[75] Inventors: Nicolaas J. van Hoboken; Roelof van de Worp, both of Deventer; Marius C. Verploegh, Bathmen, all of Netherlands

[73] Assignee: Akzo Nobel nv, Arnhem, Netherlands

[21] Appl. No.: 74,855

[22] PCT Filed: Dec. 9, 1991

[86] PCT No.: PCT/EP91/02378
§ 371 Date: Jun. 22, 1993
§ 102(e) Date: Jun. 22, 1993

[87] PCT Pub. No.: WO92/10530
PCT Pub. Date: Jun. 25, 1992

[30] Foreign Application Priority Data

Dec. 13, 1990 [EP] European Pat. Off. ......... 90203306.7

[51] Int. Cl.$^5$ ............................ C08K 5/56; C08K 5/39
[52] U.S. Cl. .................................... 523/122; 424/409; 424/417; 424/419; 424/420
[58] Field of Search ................ 523/122; 424/409, 419, 424/420, 417; 106/15.05, 18.29, 18.3, 18.31, 18.33, 18.36

[56] References Cited

U.S. PATENT DOCUMENTS

| | | | |
|---|---|---|---|
| 3,864,468 | 4/1975 | Hyman | 424/16 |
| 4,086,297 | 6/1988 | Rei et al. | 524/330 |
| 4,663,359 | 5/1987 | Rei | 523/122 |

FOREIGN PATENT DOCUMENTS

| | | |
|---|---|---|
| 835936 | 3/1970 | Canada . |
| 364159 | 4/1990 | European Pat. Off. . |
| 1288790 | 2/1969 | Fed. Rep. of Germany . |
| 2332765 | 6/1977 | France . |

OTHER PUBLICATIONS

George Tirpak: SPE Journal, Jul. 1970, vol. 26, pp. 26–30.

*Primary Examiner*—Veronica P. Hoke
*Attorney, Agent, or Firm*—Ralph J. Mancini; Louis A. Morris

[57] ABSTRACT

A microbiocide-containing concentrate for use in thermoplastic polymers as well as in plastisols, is disclosed. The concentrate is primarily solid at ambient conditions and comprises from 1–30 wt% of a microbiocide, a polymer plasticizer and up to 20 wt% of a thermoplastic resin. These concentrates are primarily useful as masterbatch compositions used for incorporation into polymers in order to protect said polymers from fungal or bacterial attack. Along these lines, the present document also discloses processes for incorporating these materials into a polymer or plastisol, and polymers or plastisols made by these processes.

7 Claims, No Drawings

PRIMARILY SOLID CONCENTRATE WHICH CONTAINS A BIOCIDE

BACKGROUND OF THE INVENTION

The present invention relates to a concentrate which contains a biocide and is primarily solid under ambient conditions. By primarily solid is meant solid, wax-like or having another non-gas and non-liquid appearance, such as a gel or paste composition.

Polymer compositions are protected against fungal or bacterial attack by the incorporation therein of a microbiocide to prevent deterioration of the polymer composition due to microbiological attack on the susceptible portion of its components. For example, German Patent DE 1,288,790 discloses the incorporation of urea or thiourea compounds, optionally together with a plasticizer, into polymers to impart antimicrobiocidal properties to the polymers. Furthermore, U.S. Pat. No. 3,864,468 discloses the incorporation of microbiocides, such as 10,10'-oxybisphenoxyarsine (OBPA), into plastisols which may comprise liquid plasticizers, such as dioctylphthalate.

In order for the microbiocide to be effective in the polymer composition, it is necessary that it be compatible therewith and uniformly dispersable therein to avoid the formation of areas within the polymer which contain insufficient biocide to prevent polymer deterioration.

To avoid toxicological problems related to the handling of the pure microbiocide, microbiocides are presently added to polymer compositions as a microbiocide-containing concentrate. Said concentrate can take different forms, such as: a liquid, a powder, or a non-powdery solid.

Liquid concentrates are usually based on a plasticizer which is liquid at ambient conditions in combination with a cosolvent. By ambient conditions is meant: standard pressure and room temperature (about 20°–30° C.). Without a cosolvent only low concentrations of the microbiocide can be obtained due to the low solubility of commonly used microbiocides in liquid plasticizers. Said cosolvent, however, may destabilize the concentrate or adversely effect the polymer composition with which it is to be mixed. A further problem arises from the fact that it is difficult to completely remove a liquid concentrate from packaging used for transport or storage, so that unless it can be reused or cleaned, this packaging becomes toxic waste.

Problems related to the toxicity of such compositions can be overcome by incorporating the microbiocide in a solid composition in such a way that it is immobilised under conditions that allow transport, storage, and the like. The following two ways of doing this were developed in the past.

U.S. Pat. No. 4,086,297 describes a method of making a concentrate to be incorporated into a second, polymeric composition, which concentrate comprises a homogeneous, melt-blended mixture of a biocide and at least 24 wt. % of a solid thermoplastic resin. This concentrate, however, cannot be added successfully to a plastisol because of its relatively high melting point and low solubility therein.

U.S. Pat. No. 4,663,359 describes a method of making a powdery concentrate in which a microbiocide is absorbed on a porous resin powder. Said concentrate is said to be mixable with a plastisol, however, it has been found that such dry blends are not universally compatible with pastisols. In other words, it is necessary to prepare various different types of dry blends in order to obtain the desired compatibility with plastisols. A plastisol can, therefor, only be adequately protected against fungal or bacterial attack if more of the concentrate is added than would be needed in case of a homogeneous distribution, thereby increasing the toxicity of the plastisol. Accordingly, a need exits for a microbiocide concentrate which can be used to make a homogeneous distribution of a microbiocide in a plastisol.

Further, the powdery concentrate is also susceptible to the formation of fines which may lead to a dust hazard. Thus, there is also a need for a solid masterbatch formulation which is not susceptible to the formation of fines. These and other objects of the invention will be apparent to one of oridinary skill in the art from the summary and detailed description which follow.

SUMMARY OF THE INVENTION

The present invention provides a primarily solid concentrate comprising a microbiocide which can be homogeneously distributed in a plastisol, and does not have the disadvantages of the prior art products previously mentioned. Other applications, such as the protection of non-plastisol plastics, are also possible. If the concentrates according to the invention are to be melt-blended with polymers, care should be taken not to use concentrates which will degrade at the melting temperature of the polymer.

The invention is characterized by the fact that the concentrate comprises:

- 1–30 wt. % of a microbiocide selected from the group consisting of phenoxyarsene compounds, copper compounds, and zinc compounds having microbiocidal activity,
- at least one plasticizer which is solid under ambient conditions in a sufficient amount to act as a carrier for the microbiocide, and
- 0–20 wt%, of a thermoplastic resin. Other aspects of the invention include a process for incorporating microbiocide in a polymer, as well as, in a plastisol.

DETAILED DESCRIPTION OF THE INVENTION

A concentrate according to the present invention can be prepared by heating a plasticizer which is solid under ambient conditions, to a temperature at or above its reelting point and mixing a microbiocide material in the melted plasticizer until a homogeneous mixture is obtained. The homogeneous mixture is then rapidly cooled to room temperature to produce a solid, microbiocide-containing concentrate. This concentrate is preferably particulated in order to render it easier to handle. Particulation can be done for example, by pelletization, flaking or granulation.

At any stage during the process of making the concentrate, typical additives used in polymer masterbatches may be incorporated into the concentrate. For example, coloring agents, surface active agents, diluents, anti-dusting agents and small amounts of polymer may all be employed as additives to the concentrate. Said additives should be compatible with the plasticizer, the microbiocide, and the polymer or the plastisol to which the concentrate will later be added. These additives may influence the melting point of the concentrate and thus care should be taken to avoid lowering the melting point of the concentrate to below ambient temperature by incorporation of additive(s) therein.

The solid plasticizers which can be used must be compatible with the polymer composition with which they are to be mixed. This can be easily accomplished by the selection of known solid plasticizers for the polymer which is to be protected from microbiocidal attack. Such plasticizers should also exhibit a low toxicity to avoid producing concentrates having an unacceptably high toxicity. Useful plasticizers include materials which are solid under ambient conditions and which are known to be polymer plasticizers. For example glycols, $C_{16}$–$C_{22}$ fatty alcohols, $C_8$–$C_{22}$ fatty acids, phthalates and phosphates may be used. More preferred plasticizers are those which melt between about 40° C. and 110° C. such as, for example, triphenyl phosphate (TPP), dicyclohexyl phthalate (DC, HP), stearic acid, 1-hexadecanol, 1-octadecanol, 1-tetradecanol, chlorinated paraffinic hydrocarbons and polyethylene glycols. The advantages of selecting plasticizers which melt in this range are that only very small amounts of the microbiocide are vaporized at such low temperatures and thus the risk to workers making the concentrate is reduced when compared with the preparation of solid masterbatches from PVC wherein the microbiocide must be heated to much higher temperatures, and that the resultant concentrates can be remelted at relatively low temperatures. Of course, mixtures of solid plasticizers are also within the scope of the present invention.

A sufficient amount of the plasticizer must be employed to act as a carrier material for the microbiocide. The exact amount of plasticizer needed will depend upon the type and concentration of the microbiocide as well as the types and amounts of other additives which may be present in the concentrate. Usually, in excess of the minimum amount of plasticizer will be employed in the concentrate in order to ensure that the toxicity level remains low. Thus, with the most preferred solid plasticizers, namely TPP and DCHP it is possible to make concentrates with 40% of a microbiocide, based on the plasticizer. However, such high concentrations of microbiocide are undesirable since the concentrate will be somewhat toxic. Accordingly, it is preferred to make concentrates containing 1–30 wt. % microbiocide, and more preferably from 4–10 wt. % microbiocide, based on the concentrate. These concentration ranges are generally higher than those obtainable by employing liquid plasticizers wherein concentrations of 1–4 wt. % are generally employed. Thus, the present invention provides the ability to employ a smaller volume of masterbatch which contains a larger concentration of the microbiocide than could be safely incorporated in commercially available liquid masterbatches.

The microbiocide is a biocide which is also a solid under ambient conditions. The microbiocides to be used in the present invention are phenoxarsene compounds like 10,10'-oxybisphenoxarsine (OPBA), copper compounds such as copper VIII hydroxy choline and various zinc dithiocarbamates. OBPA, and materials like it, are preferred because they are solid and they provide sufficient microbiocidal activity even at low concentration levels.

In some cases it may be desirable to add a small amount of thermoplastic, resin to the concentrate. Generally, this resin will be added to the melted plasticizer in powder form at a temperature high enough to ensure the dissolution of the resin in the concentrate. This thermoplastic resin is an optional component in the concentrate and may be added in amounts of from 1 up to 20 wt. %, based on the concentrate. If larger amounts of the resin are employed, the resulting concentrate will suffer from the disadvantage that it will no longer be useful in plastisols due to its high melting point and lowered solubility in the plastisol.

The concentrate of the present invention is useful as a polymer masterbatch for protecting polymers from fungal or bacterial attack. Standard masterbatching methods can be employed to incorporate the present concentrates into polymers. Further, the present composition is particularly advantageous since it may also be applied in plastisol applications.

To use the present masterbatches in plastisols, the concentrate is dissolved in the plastisol under mild heating. The preferred plasticizers, TPP and DCHP are quite good in plastisol applications since concentrates made with these plasticizers can be dissolved quickly and exhibit excellent compatibility in standard plastisols such as those based on dioctylphthalate (DOP). Once the concentrate is dissolved in the plastisol, standard plastisol application techniques can be employed to provide coatings which are protected against bacterial and fungal attack.

The following examples are presented to further illustrate the present invention and are not to be construed as limiting the scope of the invention in any way.

EXAMPLES 1–8

These examples illustrate how concentrates according to the invention are made. Each of the formulations set forth below in Table I was prepared by:
(i) heating the plasticizer to a temperature somewhat above its melting point,
(ii) mixing the microbiocide in the melted plasticizer with stirring until it is dissolved,
(iii) if additives are used, mixing the additives in the mixture, and
(iv) cooling the resulting concentrate down to below its melting point in order to let it solidify.

TABLE I

| Concentrate No. (wt. %) | 1 | 2 | 3 | 4 | 5 | 6 | 7 | 8 |
| --- | --- | --- | --- | --- | --- | --- | --- | --- |
| OBPA | 5.0 | 5.0 | 5.0 | 5.0 | 5.0 | 5.0 | 5.0 | 5.0 |
| TPP | 95.0 | 85.0 | 85.0 | 85.0 | 47.5 | — | — | — |
| DCHP | — | — | — | — | — | 85.0 | 75.0 | 47.5 |
| stearic acid | — | 10.0 | — | — | — | — | — | — |
| glyceroltristearate | — | — | 10.0 | — | — | — | — | — |
| epoxidised palm oil | — | — | — | 10.0 | — | — | — | — |
| hexadecanol | — | — | — | — | 47.5 | 10.0 | — | — |
| paraffin | — | — | — | — | — | — | 20.0 | — |
| octadecanol | — | — | — | — | — | — | — | 47.5 |
| melting point (°C.) | 48–51 | 42–44 | 48–50 | 47–49 | 42–46 | 42–60 | 46–62 | 50–52 |

EXAMPLES 9–26

A number of solid masterbatch formulations were prepared based on 5 wt. % of microbiocide and 95 wt. % of plasticizer. These formulations are listed in Table II.

These formulations were prepared by dissolving the microbiocide at about 120° C. in the plasticizer followed by crystallization of the masterbatch according to the procedure of Examples 1–8. All of these formulations exhibited good crystallization behavior indicating a uniform distribution of microbiocide in the solid plasticizer as well as sufficient solubility of the microbiocide in the plasticizer to prepare 5 wt. % solutions.

TABLE II

| Exper. No. | Fungicide (%) | Type | Carrier (%) | Type | Melting range (C.) |
|---|---|---|---|---|---|
| 9 | 5.0 | OBPA | 95.0 | 1-Hexadecanol | 48–50 |
| 10 | 5.0 | Copper (8) | 95.0 | 1-Octadecanol | 56–58 |
| 11 | 5.0 | CPA | 95.0 | 1-Octadecanol | 56–58 |
| 12 | 5.0 | OBPA | 95.0 | 1-Octadecanol | 56–58 |
| 13 | 5.0 | ZDMC | 95.0 | 1-Octadecanol | 56–58 |
| 14 | 5.0 | OBPA | 95.0 | 1-Tetradecanol | 37–38 |
| 15 | 5.0 | OBPA | 95.0 | Cereclor S-70 | 58–70 |
| 16 | 5.0 | Copper (8) | 95.0 | Polyethylene glycol 4000 | 54–58 |
| 17 | 5.0 | CPA | 95.0 | Polyethylene glycol 4000 | 54–58 |
| 18 | 5.0 | OBPA | 95.0 | Polyethylene glycol 4000 | 54–58 |
| 19 | 5.0 | Copper (8) | 95.0 | Stearic Acid | 67–69 |
| 20 | 5.0 | CPA | 95.0 | Stearic Acid | 67–69 |
| 21 | 5.0 | OBPA | 95.0 | Stearic Acid | 67–69 |
| 22 | 5.0 | Copper (8) | 95.0 | Triphenylphosphate | 48–51 |
| 23 | 5.0 | CPA | 95.0 | Triphenylphosphate | 48–51 |
| 24 | 5.0 | OBPA | 95.0 | Triphenylphosphate | 48–51 |
| 25 | 5.0 | ZDBC | 95.0 | Triphenylphosphate | 48–51 |
| 26 | 5.0 | ZDMC | 95.0 | Triphenylphosphate | 48–51 |

Copper (8) = Copper (8) hydroxy chinoline
CPA = 10-chlorophenoxarsine
OBPA = 10,10'-oxy bis phenoxarsine
ZDBC = zinc dibutyl dithiocarbamate
ZDMC = zinc dimethyl dithiocarbamate
Cereclor S-70 = chlorinated paraffinic hydrocarbons (ex. ICI)

We claim:

1. A concentrate which contains a biocide and is primarily solid under ambient conditions, which comprises
   1–30 wt. % of a microbiocide selected from the group consisting of phenoxyarsene compounds, copper compounds and zinc compounds, having microbiocidal activity,
   a plasticizer which is solid under ambient conditions, in a sufficient amount to act as a carrier for the microbiocide, and
   0–20 wt. % of a thermoplastic resin.

2. The concentrate according to claim 1, wherein the phenoxyarsene compound is 10,10'-oxybisphenoxyarsine.

3. The concentrate according to claim 1, wherein the plasticizer is selected from the group consisting of $C_8$–$C_{22}$ fatty acids, $C_{16}$–$C_{22}$ aliphatic alcohols, polyethylene glycols, phthalates and phosphates.

4. The concentrate according to claim 3, wherein the plasticizer is selected from the group consisting of triphenylphosphate, dicyclohexylphthalate, 1-hexadecanol, 1-octadecanol, 1-tetradecanot, chlorinated paraffinic hydrocarbons, polyethylene glycol and stearic acid.

5. The concentrate according to claim 1, which comprises from 1–20 wt% of a thermoplastic resin.

6. A process of incorporating a microbiocide in a polymer, wherein the concentrate according to claim 1 is incorporated in a polymer.

7. A process of incorporating a microbiocide in a plastisol, wherein the concentrate according to claim 1 is incorporated in a plastisol.

* * * * *

UNITED STATES PATENT AND TRADEMARK OFFICE
CERTIFICATE OF CORRECTION

PATENT NO. : 5,358,979

DATED : October 25, 1994

INVENTOR(S) : VAN HOBOKEN, N., et al.

It is certified that error appears in the above-identified patent and that said Letters Patent is hereby corrected as shown below:

Column 6,
In Claim 4, line 4, "1-tetradecanot" should read "1-tetradecanol".

Signed and Sealed this

Thirteenth Day of December, 1994

Attest:

BRUCE LEHMAN

Attesting Officer     Commissioner of Patents and Trademarks